United States Patent
Morici et al.

(10) Patent No.: US 10,953,081 B2
(45) Date of Patent: Mar. 23, 2021

(54) **METHODS AND COMPOSITIONS FOR INDUCING AN IMMUNE RESPONSE TO *PSEUDOMONAS AERUGINOSA* PULMONARY INFECTIONS**

(71) Applicant: The Administrators of the Tulane Educational Fund, New Orleans, LA (US)

(72) Inventors: Lisa Ann Morici, Mandeville, LA (US); Sarah Margaret Baker, Seattle, WA (US)

(73) Assignee: The Administrators of the Tulance Educational Fund, New Orleans, LA (US)

( * ) Notice: Subject to any disclaimer, the term of this patent is extended or adjusted under 35 U.S.C. 154(b) by 0 days.

(21) Appl. No.: 16/591,599

(22) Filed: Oct. 2, 2019

(65) Prior Publication Data

US 2020/0138934 A1 May 7, 2020

Related U.S. Application Data

(60) Provisional application No. 62/740,809, filed on Oct. 3, 2018.

(51) Int. Cl.
*A61K 39/00* (2006.01)
*A61K 39/104* (2006.01)
*A61K 39/108* (2006.01)
*A61K 9/00* (2006.01)

(52) U.S. Cl.
CPC .......... *A61K 39/104* (2013.01); *A61K 9/0021* (2013.01); *A61K 39/0258* (2013.01); *A61K 2039/54* (2013.01)

(58) Field of Classification Search
CPC .................................................. A61K 39/104
See application file for complete search history.

(56) References Cited

PUBLICATIONS

Plotkin et al (Vaccines W. B. Saunders Company, p. 571) (Year: 1988).*
Merakou et al (Surgical Infections vol. 19, No. 8, pp. 757-768) (Year: 2018).*
Rello et al (Critical Care 21:22 pp. 1-13) (Year: 2017).*
Priebe et al (Expert Rev. Vaccines 13(4) pp. 507-519) (Year: 2014).*
Albert, M.J., et al., "Immunization with a Double-Mutant (R192G/L211A) of the Heat-Labile Enterotoxin of *Escherichia coli*," PLOS one, 2015, doi:10.1371/journal.pone.0142090.
Baker, S.M., "Intradermal Vaccination Induces Protective Humoral and Cellular Immunity in the Lung," Dissertation, Tulane Med Sch, submitted Dec. 8, 2016, edited Feb. 13, 2017.
Baldwin, S., et al., "Intradermal immunization improves protective efficacy of a novel TB vaccine candidate," Vaccine, 2009, 3063-3071, v. 27(23).
Frederick, D., et al., "Adjuvant selection regulates gut migration and phenotypic diversity of antigen-specific CD4+" Mucosal Immunol., Mar. 2018, pp. 549-561, v. 11(2).
Heine, S., et al., Intradermal delivery of Shigella IpaB and IpaD type III secretion proteins: Kinetics of cell recruitment and J Immunol, 2014, pp. 163-1640, v. 192(4).
Novotny L., et al., Kinetic analysis and evaluation of the mechanisms involved in the resolution of experimental nontypeable Vaccine, 2013, pp. 3417-3426, v. 31(34).
Woolard, M., et al., "Respiratory Francisella tularensis Live Vaccine Strain Infection Induces Th17 Cells and," Infection and Immunity, 2008, pp. 2651-2659, v. 76(6).
Baker, et al., Intradermal vaccination with a Pseudomonas aeruginosa vaccine adjuvanted with a mutant bacterial Adp-ribosylating . . . ,Vaccine, epub Jan. 9, 2019, p. 808-816, v 37.
Baker, et al., Immunological considerations in the development of Pseudomonas aeruginosa vaccines, Hum Vaccin Immunother. epub Sep. 5, 2019, p. 412-418, v. 16(2).

* cited by examiner

*Primary Examiner* — Albert M Navarro
(74) *Attorney, Agent, or Firm* — Laurence J. Hyman; Hyman IP Law

(57) ABSTRACT

The invention provides methods and compositions for preventing or ameliorating pulmonary infections with *Pseudomonas aeruginosa*.

20 Claims, 9 Drawing Sheets

METHODS AND COMPOSITIONS FOR INDUCING AN IMMUNE RESPONSE TO PSEUDOMONAS AERUGINOSA PULMONARY INFECTIONS

CROSS-REFERENCE TO RELATED APPLICATIONS

This application claims priority to, and the benefit of, U.S. Provisional Patent Application No. 62/740,809, filed Oct. 3, 2018, the contents of which are incorporated herein by reference for all purposes.

STATEMENT OF FEDERAL FUNDING

Not applicable.

BACKGROUND OF THE INVENTION

The mucosal surfaces of the gastrointestinal, respiratory, and genital tracts serve as the main portal of entry for most pathogens. The lack of success in the development of vaccines against some mucosal pathogens such as human immunodeficiency virus, herpes viruses, and various respiratory bacterial infections, may be partly due to the inability of current vaccine strategies to adequately stimulate multiple arms of the innate and adaptive immune systems and to target essential immune responses to infected mucosal tissues. The paucity of vaccines against pulmonary bacterial pathogens and the emerging multidrug resistance among many of these bacteria highlights the need for rational vaccine design and alternative delivery strategies for eliciting both local and mucosal immunity against this collective group of pathogens.

Pseudomonas aeruginosa is a Gram-negative, motile, rod-shaped bacterium that is ubiquitous in the environment. It is a significant human pathogen, capable of causing infections of the respiratory tract, urinary tract, skin and soft tissues, eyes, and ears, with infections occurring primarily in those patients with physical, phagocytic, or immunologic defects in host defense mechanisms. In particular, it is an etiologic agent of healthcare-associated and ventilator-associated pneumonia, chronic pulmonary infection in cystic fibrosis (CF) patients, and burn and soft tissue infections. As a nosocomial pathogen, P. aeruginosa poses an enormous burden on the health care system and is responsible for 17% of ventilator associated pneumonias and 9% of other healthcare associated pneumonias. Importantly, infection with P. aeruginosa is emerging as a healthcare crisis, with 6,700 multidrug resistant infections occurring in the United States annually. Multidrug resistance severely limits the choice and efficacy of antibiotic treatment regimens against P. aeruginosa. The increasing prevalence of drug-resistant P. aeruginosa infections has prompted the World Health Organization to list P. aeruginosa as one of the top priorities for the development of new medical countermeasures.

The genome of P. aeruginosa contains a highly conserved core genome and a highly variable accessory genome, which encodes for a broad range of transporters, transcriptional regulators, and two-component regulatory systems. The genetic diversity of P. aeruginosa provides metabolic versatility for the organism, allowing it to survive in a multitude of environments, ranging from soil and water to biofilms formed within catheters or ventilator equipment. Importantly, this genetic pliability also contributes to P. aeruginosa's multidrug resistance.

Despite the clear morbidity and mortality associated with P. aeruginosa, no vaccine has ever been licensed for the prevention of infection. This is not for lack of effort. In 1970, Alexander and Fisher published a letter citing that a P. aeruginosa LPS-based vaccine prevented mortality in burn patients. Alexander and Fisher, Am J Surg, 1970, 120:512. Since that publication, numerous attempts have been made to develop and advance a P. aeruginosa vaccine towards licensure. Historically, vaccine development for P. aeruginosa has focused on identification of protective antigens and utilization of various vaccine platforms, including live-attenuated or whole-cell inactivated strains, subunit, conjugate, and DNA vaccines. Some of these candidate vaccines produced promising results in animal models, primarily based on protective antibodies, and were advanced to clinical trials. The literature contains a number of detailed reviews of P. aeruginosa vaccine antigens and previous clinical trials, including Priebe and Goldberg, Expert Rev Vaccines, 2014, 13:507-19; Sharma et al., Human Vaccines, 2011, 7:999-1011; Worgall et al., Future Microbiol., 2012, 7:1333-5; Grimwood et al., Human Vaccines & Immunotherapeutics, 2015, 11(1):14-20; and Merakou et al., Surgical Infections, 2018, 19:757-68. Despite these attempts, no vaccine is currently on the market.

It would be useful to have additional means to reduce the infection of patients by P. aeruginosa, to reduce the severity of infection in those already infected with P. aeruginosa by increasing their immune response to the bacterium, or both. Surprisingly, the present invention fills these and other needs.

SUMMARY OF THE INVENTION

In a first group of embodiments, the invention provides methods for preventing or ameliorating a Pseudomonas aeruginosa lung infection in a subject, said method comprising intradermally co-administering to said subject P. aeruginosa outer membrane proteins (OMPs) and an Escherichia coli heat-labile enterotoxin (LT) with mutations at R192G and L211A ("dmLT"). In some embodiments, the OMPs and the dmLT are co-administered in a single formulation. In some embodiments, the intradermal administration is by microneedles. In some embodiments, the P. aeruginosa OMPs comprise OprI. In some embodiments, the P. aeruginosa OMPs comprise OprF. In some embodiments, the P. aeruginosa OMPs comprise OprG and KatA. In some embodiments, the P. aeruginosa OMPs and the dmLT are co-administered to a subject who does not have a P. aeruginosa lung infection. In some of these embodiments, the subject has cystic fibrosis. In some of these embodiments, the subject is on a ventilator. In some embodiments, the P. aeruginosa OMPs and the dmLT are co-administered to a subject who has a P. aeruginosa lung infection. In some of these embodiments, the subject has cystic fibrosis. In some of these embodiments, the subject is on a ventilator.

In a second group of embodiments, the invention provides compositions intradermal vaccination of a subject in need thereof, the composition comprising Pseudomonas aeruginosa outer membrane proteins (OMPs) and an Escherichia coli heat-labile enterotoxin (LT) with mutations at R192G and L211A ("dmLT"). In some embodiments, the composition further comprises a pharmaceutically acceptable carrier. In some embodiments, the P. aeruginosa OMPs include OprI. In some embodiments, the P. aeruginosa OMPs comprise OprF. In some embodiments, the P. aeruginosa OMPs comprise OprG and KatA.

BRIEF DESCRIPTION OF THE DRAWINGS

FIG. 1A. Three independent batches of OMPs were prepared from P. aeruginosa strain PAO1 to demonstrate reproducibility of the preparations. OMPs (1-3) were separated by SDS-PAGE and stained with Coomassie blue.

FIG. 2A. Mice were immunized with P. aeruginosa OMPs+dmLT (n=15), OMPs alone (n=10), or sham (n=10) intradermally. Antigen-specific serum IgG were measured by ELISA using microtiter plates coated with heat-inactivated P. aeruginosa. Results are expressed as EU (ELISA units) per ml. Data shown is the cumulative result of three independent experiments. ns=not significant, *p<0.05, **p<0.01 using a one way ANOVA with Tukey's multiple comparisons test. FIG. 2B shows the results of the same study, but looking at antigen-specific IgG in bronchoalveolar lavage fluid (BAL) rather than serum.

FIG. 3A. Mice (n=6 per group) were immunized with P. aeruginosa OMPs+dmLT, P. aeruginosa OMPs alone, or saline (sham) intradermally. P. aeruginosa-specific CD4+ T cell response was assessed 14 days after final immunization. Lungs were collected, dissociated, and plated into tissue culture dishes. Tissue explants were restimulated with α-CD28 and heat-inactivated P. aeruginosa followed by intracellular cytokine staining for IFN-γ. Percentage of CD4+ T cells that are CD44+ and IFN-γ+, IL-17+ or IL-4+ were analyzed. Results shown are the cumulative data from two independent experiments. ns=not significant, *p<0.05, **p<0.01 by one-way ANOVA with Tukey's multiple comparisons test. FIG. 3B shows the results of the same study as discussed in FIG. 3A, but the intracellular staining shown was for IL-17. FIG. 3C shows the results of the same study as discussed in FIG. 3A, but the intracellular staining was for IL-4.

FIG. 4A. Mice were immunized with P. aeruginosa OMPs+dmLT (n=15), P. aeruginosa OMPs (n=15), dmLT (n=15), or saline (n=9). Animals were challenged with 1.4×10$^7$ CFU delivered by oropharyngeal aspiration 14 days after immunization. P. aeruginosa OMPs+dmLT-immunized mice were significantly protected against an otherwise lethal P. aeruginosa lung infection (****p<0.0001 by log rank Mantel-Cox test). FIG. 4B shows data from the same experiment discussed with respect to FIG. 4A, but showing the weight of the mice. Immunized mice rapidly lost weight after challenge but survivors began recovering by day 3 post-infection. Data shown is the cumulative result of three independent experiments.

FIGS. 5A-H show the profile of certain cytokines during P. aeruginosa infection of mice that have first been immunized intradermally with OMPs and dmLT. FIG. 5A. Mice (n=5 per group) were immunized with P. aeruginosa OMPs+dmLT or control (dmLT alone) intradermally. All animals were challenged with 1.4×10$^7$ CFU delivered by oropharyngeal aspiration 14 days after immunization. The concentration of IFN-γ cytokine present in the BAL fluid 24 hours after infection was measured by luminex assay. Cytokine level was standardized by BAL protein content. ns=not significant, *p<0.05, p<0.01, *p<0.005 by Two-tailed t test. FIG. 5B. FIG. 5B shows the results of the same study as reported in FIG. 5A, but shows the results for the cytokine IL-17 rather than IFN-γ. FIG. 5C. FIG. 5C shows the results of the same study as reported in FIG. 5A, but shows the results for IP10 rather than IFN-γ. FIG. 5D. FIG. 5D shows the results of the same study as reported in FIG. 5A, but shows the results for the cytokine IL-2 rather than IFN-γ. FIG. 5E. FIG. 5E shows the results of the same study as reported in FIG. 5A, but shows the results for RANTES rather than IFN-γ. FIG. 5F. FIG. 5F shows the results of the same study as reported in FIG. 5A, but shows the results for IL-12p70 rather than IFN-γ. FIG. 5G. FIG. 5G shows the results of the same study as reported in FIG. 5A, but shows the results for the cytokine IL-7 rather than IFN-γ. FIG. 5H. FIG. 5B shows the results of the same study as reported in FIG. 5A, but shows the results for the cytokine IL-10 rather than IFN-γ.

FIG. 6A. Mice (n=6 per group) were immunized with P. aeruginosa OMPs+dmLT, P. aeruginosa OMPs alone, or saline (sham) intradermally. P. aeruginosa-specific CD4+ T cell response was assessed 14 days after final immunization. Lungs were collected, dissociated, and plated into tissue culture dishes. Tissue explants were restimulated with α-CD28 and heat-inactivated P. aeruginosa followed by intracellular cytokine staining. Contour plots shown are representative of examples demonstrating the percentage of CD4+ T cells that are CD44+ and producing IFN-γ.

FIG. 7 is a graph showing that vaccination did not induce significant levels of IgA. Mice were immunized with P. aeruginosa OMPs+dmLT (n=5), OMPs alone (n=5), or sham (n=5) intradermally. Antigen-specific serum IgA titers were measured by ELISA using microtiter plates coated with heat-inactivated P. aeruginosa. Results are expressed as EU (ELISA units) per ml. ns=not significant using a one way ANOVA with Tukey's multiple comparisons test.

FIG. 8 is a graph showing that there was no difference in the overall percentage of CD4+ T cells that are CD44+ between groups vaccinated with OMPs+dmLT, OMPs by themselves, or saline. Mice (n=3 per group) were immunized with P. aeruginosa OMPs+dmLT, P. aeruginosa OMPs alone, or saline (sham) intradermally. P. aeruginosa-specific CD4+ T cell response was assessed 14 days after final immunization. Lungs were collected, dissociated, and plated into tissue culture dishes. Tissue explants were restimulated with α-CD28 and heat-inactivated P. aeruginosa followed by surface staining, including CD4 and CD44. ns=not significant.

DETAILED DESCRIPTION

Figure 1A:
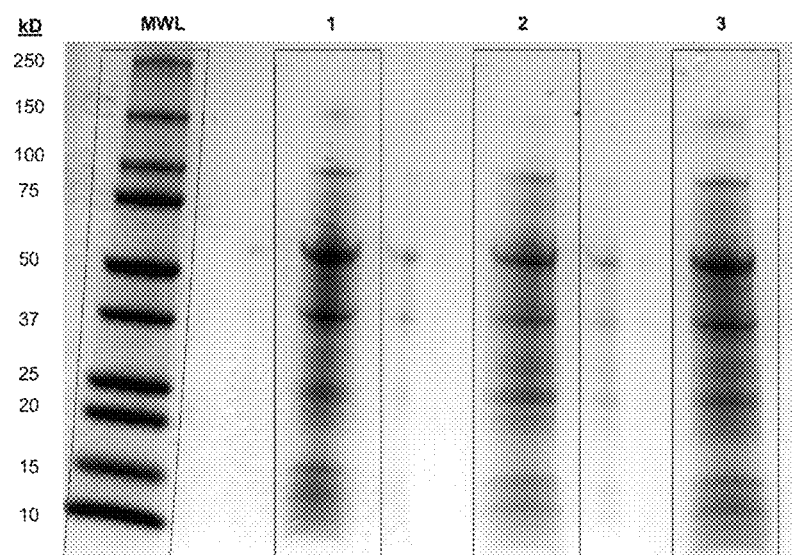
FIGS. 1A and B.

As discussed in the Background, Pseudomonas aeruginosa is an etiologic agent of healthcare-associated and ventilator-associated pneumonia, chronic pulmonary infection in cystic fibrosis (CF) patients, and burn and soft tissue infections. The development of multidrug resistance in P. aeruginosa has made infections with this organism a source of significant morbidity and mortality. Despite many experimental vaccines studies over the last several decades, no P. aeruginosa vaccine has obtained market authorization, due to an inability to achieve long-lasting protection against pulmonary infection with limited and often conflicting efficacy data.

The present disclosure provides a new approach to a *P. aeruginosa* vaccine. Surprisingly, a vaccine composed of a low dose of *P. aeruginosa* outer membrane proteins (OMPs) adjuvanted with a *Escherichia coli* (*E. coli*) heat-labile enterotoxin ("LT") with two mutations, R192G and L211A, that render it non-toxic, administered intradermally, protected against lethal *P. aeruginosa* pulmonary infection in an animal model, with 78% of immunized mice surviving pulmonary challenge. (The mutated LT is sometimes referred to herein as "dmLT"). Intradermal immunization resulted in significantly greater concentrations of antigen-specific IgG in the serum and bronchoalveolar lavage fluid than did intramuscular or subcutaneous immunization. Intradermal immunization also resulted in significantly greater concentrations of antigen-specific IgG in the serum and bronchoalveolar lavage fluid.

Further, studies underlying the present disclosure showed intradermal immunization to induce the production of IFN-γ and pathogen-specific Th1- and Th17-type CD4+ T cells in the lungs.

To our knowledge, this is the first *P. aeruginosa* intradermal vaccine to demonstrate protection against a direct pulmonary challenge in a lethal *P. aeruginosa* acute pneumonia model in an immunocompetent mouse. Additionally, this is the first *P. aeruginosa* vaccine to use dmLT as an adjuvant to enhance immune responses. The combination of OMPs, dmLT, and intradermal injection is believed to be responsible for the success of the vaccine.

The ability of the inventive vaccines and methods to induce Th17 type CD4+ T cells in the lungs indicates that they will be useful in protecting patients. It is further thought that these results show that the inventive vaccines and methods will be particularly useful in protecting subjects particularly vulnerable to *P. aeruginosa* pulmonary infections, such as CF patients and persons on ventilators.

Further, the immunological response that protects immunized subjects from infection with *P. aeruginosa* is expected to also help reduce the population of *P. aeruginosa* in an individual already infected with the organism. Thus, the inventive vaccines and methods are expected to be able to help reduce the number of *P. aeruginosa* organisms in a subject suffering from a *P. aeruginosa* infection, such as a pulmonary infection, thereby reducing the severity of the infection and ameliorating its symptoms. Accordingly, the inventive vaccines and methods can be used to treat subjects already suffering from an infection with *P. aeruginosa* and, in particular, with a pulmonary infection, such as pneumonia caused by *P. aeruginosa*.

Definitions

The terms "effective amount" or "therapeutically effective amount" of a composition, as provided herein, refer to a nontoxic but sufficient amount of the composition to provide the desired therapeutic effect, or an amount sufficient to effect treatment of the subject, as defined below. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

The phrase "pharmaceutically acceptable," in connection with administration of a substance to a human refers to a substance that is generally safe for human pharmaceutical use. In connection with administration to a non-human animal of a particular species, it refers to a substance that is generally safe and acceptable to a non-human animal of the species in question.

As used herein, the terms "pharmaceutically acceptable carrier" and "pharmaceutically acceptable vehicle" are interchangeable and refer to a fluid vehicle for containing OMP and enterotoxin compositions that can be injected into a host without adverse effects or administered to a host without adverse effects, depending on the intended route of administration. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

*Pseudomonas aeruginosa*

As discussed in the Background, *Pseudomonas aeruginosa* (sometimes referred to herein as "PA") is a Gram-negative, motile, rod-shaped bacterium that is ubiquitous in the environment. *P. aeruginosa* is a quintessential opportunistic pathogen and the etiologic agent of several potentially life-threatening infections, including healthcare-associated and ventilator-associated pneumonia, chronic pulmonary infection in cystic fibrosis (CF) patients, and burn and soft tissue infections. The increasing prevalence of drug-resistant *P. aeruginosa* infections has prompted the World Health Organization to list *P. aeruginosa* as one of the top priorities for the development of new medical countermeasures.

*P. aeruginosa* PAO1 is a derivative of the PAO clinical isolate and is the most commonly used strain for *P. aeruginosa* research (Klockgether et al., Frontiers in Microbiology, 2011, vol. 2, article 150, doi.org/10.3389/fmicb.2011.00150). The genome of PAO1 was first sequenced in 2000 (see, Stover, et al., Nature, 2000, 406 (6799):959-964), and is available in GenBank under accession number NC_002516. The genome of *P. aeruginosa* contains a highly conserved core genome and a highly variable accessory genome, which encodes for a broad range of transporters, transcriptional regulators, and two-component regulatory systems. The genetic diversity of the organism provides metabolic versatility, allowing it to survive in a multitude of environments, ranging from soil and water to biofilms formed within catheters or ventilator equipment. Importantly, this genetic pliability also contributes to *P. aeruginosa*'s multidrug resistance.

*P. aeruginosa* uses a multi-faceted approach to survive within a host, including cell surface molecules that aid in attachment to host cells and bacterial secretion systems that produce toxins and effector proteins to evade or modulate the host immune response (ie. type three secretion systems). Once *P. aeruginosa* enters an immune-compromised individual, the bacterium uses flagella for motility and numerous type IV pili to mediate attachment to cell surfaces. The surface components of the organism, including lipopolysaccharide (LPS) and the exopolysaccharide alginate, mediate bacterial adherence to host cells and facilitate bacterial survival within the host. Alginate is believed to protect the bacterium in harsh environments and from oxidative stress and immunological attack, such as that encountered in the CF lung. Alginate also contributes to biofilm formation and enables the organism to persist in the lungs of individuals with CF, leading to chronic infection, enhanced morbidity, and worsening prognosis for these patients. The outer membrane of *P. aeruginosa* also contains several proteins that function to stabilize and protect the bacterium, including those that control or facilitate molecular transport across the membrane barrier. These proteins are highly conserved across P. aeruginosa serogroups and remain phenotypically stable during biofilm formation. Collectively, these surface and secreted components can modulate the host immune system, damage host tissues, and dictate bacterial virulence. For these reasons, many of these components are the natural target of adaptive immune responses and have been explored as vaccine candidates. A comprehensive review of P. aeruginosa virulence factors and survival strategies in the human host is set forth in, e.g., Moradali et al., Front Cell Infect Microbiol 2017; 7:39.

The multitude of virulence factors possessed by P. aeruginosa contributes to its versatility and the diverse manifestations of disease associated with P. aeruginosa infections. P. aeruginosa is a significant human pathogen, capable of establishing infections in the respiratory tract, urinary tract, skin and soft tissues, eyes, and ears. Infections occur primarily in patients with physical, phagocytic, or immunologic defects in host defense mechanisms. As a nosocomial pathogen, P. aeruginosa infections pose a strenuous burden on the health care system and are responsible for 17% of ventilator associated pneumonias, 9% of other healthcare associated pneumonias, 10% of catheter-associated urinary tract infections, 4% of central line-associated blood stream infections, and 6% of surgical site infections. P. aeruginosa is also the predominant bacteria infecting the lungs of CF patients, causing severe morbidity and mortality in these individuals.

Additionally, P. aeruginosa is becoming an increasingly common pathogen isolated from personnel returning from Iraq and Afghanistan with combat-related infections. Off the battlefield, P. aeruginosa continues to pose a challenge in burn wound infections, with antibiotic resistance rapidly increasing in this patient population. Cancer patients who suffer from chemotherapy-induced neutropenia are also a growing clinical group at high-risk for P. aeruginosa infections, including pneumonia and bacteremia.

Immunity to P. aeruginosa has been most extensively studied in CF patients. Once colonized with P. aeruginosa, CF patients mount antibody responses to many P. aeruginosa antigens. CF adults who were not chronically colonized with P. aeruginosa possessed antibodies to alginate that were shown to mediate opsonophagocytosis, indicating some protective potential. However, in most cases, antibodies are unable to sufficiently curb the spread of infection, suggesting that infection-induced antibodies do not confer sufficient protection against future P. aeruginosa infections in these patients. Clinical studies comparing CF patients with and without chronic infection observed that patients with persistent P. aeruginosa lung infection had an immune response predominantly of the Th2 type, whereas patients with the highest production of IFN-γ, a Th1 cytokine, had the best lung function, indicating that Th1 T cells may be essential mediators of protection. Another study assessing CF patients chronically infected with P. aeruginosa found significantly higher levels of pulmonary Th2 cells and the Th2 cytokines IL-4, IL-13, and thymus and activation-regulated chemokine (TARC, also known as CCL17) in bronchoalveolar lavage fluid and lower levels of IFN-γ compared with uninfected patients with CF and healthy controls. Bronchoalveolar lavage fluid levels of these Th2 cytokines correlated inversely with pulmonary function. In a prospective study of children with CF, TARC was significantly increased in patients who developed P. aeruginosa infection during the 2 years of study. Assessment of cytokine expression in mucosal bronchial biopsies of CF patients found the highest expression of TGF-β and IFN-γ in CF patients with only mild disease and a history of infrequent exacerbations, as compared to those patients with frequent acute exacerbations and chronic infection. Despite the cumulative findings described above, it is important to note that CF patients can display tremendous heterogeneity in their immune response to P. aeruginosa. Moreover, inherent defects in anti-bacterial mechanisms may diminish the effectiveness of adaptive immunity in the CF lung.

Animal models of pulmonary infection also demonstrate a protective role for Th1 cells. Resistance to re-infection with P. aeruginosa in mice was associated with a Th1 response, demonstrated by a higher IFN-γ/IL-4 ratio 31. In a vaccine study utilizing a live-attenuated P. aeruginosa strain, passive transfer of purified IgG failed to protect mice against heterologous strain challenge, whereas active immunization was protective. Additionally, mice that have a Th1 bias are better protected compared to mice with a clear Th2 bias. These results suggest that cellular immunity, and in particular Th1 T cell immunity, may play a key role in protection against P. aeruginosa infection.

Additionally, Th17 cells have sparked significant research since their discovery, particularly due to their role in the mucosal immune response against pulmonary pathogens. The multiple downstream effects of IL-17 indicate that the Th17 response strikes a precarious balance between protecting the mucosal surfaces and facilitating destructive tissue inflammation. IL-17 regulates granulopoesis by regulating production of G-CSF and also actively recruits neutrophils to sites of infection through the induction of CXC cytokines at sites of inflammation. IL-17 is also induced in the lung in response to mucoid P. aeruginosa infection. Significantly higher levels of IL-17 are found in bronchial secretions of CF patients following acute pulmonary exacerbations and IL-17 has been shown to be required for the control of chronic P. aeruginosa pulmonary disease in mouse models. Importantly, it is known that the secretion of IL-17A by CD4+ T cells is essential for the rapid recruitment of neutrophils to the lungs. Neutrophils are essential for the efficient killing of P. aeruginosa during acute pulmonary infection, indicating that Th17 cells, like Th1 cells, may be important for the complete control of P. aeruginosa.

Outer Membrane Proteins of P. aeruginosa

Outer membrane proteins (OMPs) of P. aeruginosa have been studied for decades. Information regarding a number of P. aeruginosa OMPs is collated and reviewed in, for example, Hancock et al., "Outer membrane proteins of Pseudomonas," Molecular Microbiology (1990) 4(7), 1069-1075. Montor et al., Infection and Immunity, 2009, 77(11): 4877-4886, reported what they termed a comprehensive study of all 262 outer membrane and exported P. aeruginosa PAO1 proteins by a modified protein microarray methodology. Hancock and Brinkman (Annual Rev Microbiol, 2002, 56:17-38) reviewed 3 major families of P. aeruginosa porins, including 19 members of the OprD family, 18 members of the OprM family, and 35 members of the TonB interacting family of porins.

A combination of recombinant OprF and Outer Membrane Protein I (OprI) as a vaccine candidate was reported in von Specht et al., J. Biotechnol., 1996, 44(1-3):145-153. A chimeric protein combining the receptor binding and membrane translocation domains of Pseudomonas exotoxin A (PE) with the outer membrane proteins I and F was tested as a vaccine in an animal model and found to provide significant protecting against infection with PA PA01. See, Chen et al., Appl Microbiol Biotechnol. 1999, 52(4):524-33 Immunization of mice with PA OMP-F was reported by Ahmadi et al., J Infect Dev Ctries., 2012, 6(10):721-6, to provide protection against subsequent challenge. Human IgG to OMPs was reported to be cross-protective to heterologous strains of PA in Lee et al., FEMS Immunol Med Microbiol. 1999, 25(4):339-47 and Lee et al., Vaccine. 1999, 12; 18(7-8):665-74.

The OMPs included in the vaccine formulations used in studies reported in this disclosure include OprF and OprI, which are conserved across *P. aeruginosa* strains. The conserved nature of these OMPs is important, as *P. aeruginosa* patients can be colonized with many different strains (Wolz et al. Epidemiology and Infection, 1989, 102(2): 205-214), and therefore cross-strain protection is advantageous. Additionally, the vaccine preparation in the studies contained other potentially protective antigens, including OprG and KatA, proteins which may play a role in protection against chronic *P. aeruginosa* infection in CF patients (Moore et al., Human Vaccines & Immunotherapeutics, 2013, 9(3):506-514). Studies conducted in the course of the present work demonstrated that the vaccine was safe in mice at both 1 μg and 10 μg doses.

OMPs suitable for use in embodiments of the invention can be purified from cultures of *P. aeruginosa* or can be produced by recombinant means. As noted in the preceding section, the entire genome of *P. aeruginosa* has been publicly available since 2000 and is accessible on GenBank. It is expected that persons of skill can isolate or can clone and produce by recombinant means any particular OMP of *P. aeruginosa* they wish. Cloning of OprI is described in Lin et al., J Biol Chem. 2010, 285(12): 8985-8994. Isolation of OprJ, OprD, OprN, and OprM is described in, for example, Masuda et al., Antimicrob Agents Chemother. 1995, 39(3): 645-649. Cloning of OprQ is reported in Arhin and Boucher, Microbiol., 2010, 156(Pt.5): 1415-23.

*E. coli* Enterotoxin and the dmLT Mutant

According to the website of the Centers for Disease Control and Prevention: "Enterotoxigenic *Escherichia coli* (*E. coli*), or ETEC, is an important cause of bacterial diarrheal illness. Infection with ETEC is the leading cause of travelers' diarrhea and a major cause of diarrheal disease in lower-income countries, especially among children." Certain strains of enterotoxigenic *E. coli* produce a heat-labile enterotoxin ("LT"). It has been established for many years that LT induces cAMP accumulation through binding to host cell ADP-ribosylation factor ("ARF") to initiate ADP-ribosylation of Gsa, leading to irreversible activation of adenylate cyclase and increased production of intracellular cAMP, which ultimately leads to secretory diarrhea.

LT has an $AB_5$ structure with non-covalently attached A- and B-subunits. The A-subunit causes the enterotoxic effects of the holotoxin, while five B ("binding")-subunits assemble to form a pentameric structure which is responsible for cellular binding and internalization. The 28 kD A-subunit is susceptible to cleavage by trypsin, resulting in a 21 kD A1 domain. The 56 kD B-subunit pentamer is more proteolytically stable and only breaks down into 11 kD monomers upon boiling.

The nucleic acid and amino acid sequences of both the A and the B subunits have been known for decades, as exemplified by Yamamoto et al., J. Bacteriol 1987, 169:1352-57, which presents the nucleic acid and amino acid sequences of both the A and the B subunits for the form found in human isolates (shown in the paper as "LTh").

As the name implies, the double mutant LT ("dmLT") used in the inventive methods and compositions is a version of LT with two mutations in the A subunit: R192G/L211A. Production and characterization of the dmLT mutant is well known (see, e.g., Norton et al., Clin. Vaccine Immunol. 2011, 18:546-551) and the mutant has been tested in pre-clinical studies as an adjuvant in a variety of vaccine formulations, particularly for oral administration. See, e.g., Norton et al., Infect. Immun. 2012, 80:2426-2435; Norton et al., Vaccine. 2015, 33:1909-1915; White et al., J Immunol Methods. 2017, 451: 83-89; Holmgren et al., Vaccine. 2013, 7; 31(20):2457-64.

Formulations

Making intradermal oral dosage forms is well known in the art, and it is expected that persons of skill are familiar with the considerable literature and guidance that exists, as exemplified by texts such as Gennaro, A., REMINGTON'S PHARMACEUTICAL SCIENCES, $18^{th}$ Ed., (1990), Rowe, Shesky and Quinn, eds. HANDBOOK OF PHARMACEUTICAL EXCIPIENTS, $6^{th}$ Ed. (Pharmaceutical Press, London, 2009) and L. Allen, ed., REMINGTON: THE SCIENCE AND PRACTICE OF PHARMACY, vols I and II, $22^{nd}$ Ed. (Pharmaceutical Press, Philadelphia, 2012).

In addition to the OMPs, dmLT, and carrier of choice, the formulations may include one or more pharmaceutically acceptable excipients, stabilizers, binders, lubricants, fillers, buffers, antioxidants, preservatives, monosaccharides, disaccharides, and other sugars or carbohydrates, including glucose, mannose, sucrose, mannitol, trehalose or sorbitol.

Route, Dosing, and Administration

Almost every vaccine currently licensed in the United States and administered systemically is administered by intramuscular injection (see, e.g., Hamborsky, J., & Kroger, A. (2015). Epidemiology and prevention of vaccine-preventable diseases, E-Book: The Pink Book.). Conversely, the lack of success seen in the development of vaccines against mucosal pathogens such as HIV, herpes viruses, *Mycobacterium* species, and *P. aeruginosa*, may be attributed in part to the inability of systemic immunization to adequately activate multiple arms of the innate and adaptive immune system and target responses to the mucosal tissue being infected. The studies reported herein indicate that intradermal administration of PA OMPs adjuvanted with dmLT not only activates multiple arms of the immune system and targets responses to mucosal tissue, but also drives a cellular immune response in pulmonary tissues.

For purposes of the inventive methods, an "effective amount" of a co-administration of PA OMPs and dmLT refers to an amount of PA OMPs and dmLT that, alone or in combination with further doses, produces the desired response. With respect to use as a prophylactic vacine, e.g., in raising an immune response to *P. aeruginosa*, such as inducing an antibody response, a T cell response, or both, when co-administered by intradermal injection, an effective amount is an amount that raises the desired immune response in the subject. In studies underlying the present disclosure, mice were immunized with 1 μg of PA OMPs adjuvanted with 1 μg dmLT and 78% of the mice were protected against pneumonia when subsequently challenged with $7 \times 10^6$ CFU *P. aeruginosa*. It is expected that the amounts of each agent needed to raise an immune response to PA infection in larger mammals, such as humans, will be similarly small.

For use in ameliorating or otherwise treating a subject with a pulmonary infection with PA, the "therapeutically effective amount" will generally be the same as that used for prophylactic use. In studies underlying the present invention, no significant difference was seen in anti-pseudomonal serum or bronchial lavage fluids IgG, or in IFN-γ or IL-17A cytokine production by CD4+ antigen-experienced T cells in the lungs or mediastinal lymph nodes when immunizing with only 1 μg P. aeruginosa OMPs with dmLT compared to 10 μg P. aeruginosa OMPs with dmLT.

Intradermal administration is known in the art, and delivery of intradermal vaccines can be made either through traditional means or newer methods, such as disposable jet injectors or microneedles. See, e.g., Hickling, J., & Jones, R. (2009). Intradermal delivery of vaccines: a review of the literature and the potential for development for use in low- and middleincome countries. Program for Appropriate Technology in Health (PATH); Prausnitz et al., "Microneedle-Based Vaccines," in R. Compans and W. Orenstein, eds., VACCINES FOR PANDEMIC INFLUENZA, Springer-Verlag, Berlin (2009); Harvey et al., Pharm. Res., 2011, 28(1):107-116; Van Damme et al., Vaccine, 2009, 27(3):454-59; Alarcon et al., Clin. Vaccine Immunol. 2007, 14(4):375-81; Tuan-Mahmoood et al., Europ. J. Pharm. Sci., 2013, 50(5):623-637; Donnelly et al., Drug Delivery, 2010, 17(4): 187-207.

EXAMPLES

Example 1

This Example sets forth methods and materials used in the studies discussed below.

Animal Care Studies underlying the present disclosure were performed in strict accordance with the Guide for the Care and Use of Laboratory Animals of the National Institutes of Health (NIH Publications No. 8023, revised 1978). The protocols were approved by the Tulane University Institutional Animal Care and Use Committee. For survival studies, death was not used an as endpoint. Mice were humanely euthanized once they displayed >20% weight loss, paralysis, or were unresponsive to handling. Mice were observed at least three times daily, including weekends. Euthanasia was performed in mice by $CO_2$ overdose and confirmed by cervical dislocation.

Bacterial strain. The PAO1 strain of P. aeruginosa was used for all studies. PAO1 is a derivative of the PAO clinical isolate and is a commonly used strain for P. aeruginosa research. To prepare P. aeruginosa for mouse challenge experiments, a single colony of PAO1 was inoculated into 5 ml Tryptic Soy Broth (TSB, Fluka Analytical) and incubated overnight shaking at 233 rpm at 37° C. The optical density (OD) was then measured and an OD600 of 2.0 was added to 20 ml TSB. The culture was incubated for 4 hours shaking at 233 rpm at 37° C. until an OD600 of 3.5-4.0 was reached. The bacteria were pelleted and resuspended in PBS. Bacterial concentration was adjusted to obtain a concentration of $2.8 \times 10^8$ CFU/ml.

To prepare heat-inactivated bacteria, two primary overnight cultures of P. aeruginosa in 5 ml LB each were grown to confluency and two secondary overnight cultures were made, diluting the primary culture 1:10 in 50 ml of LB. After overnight incubation at 37° C. with shaking at 233 rpm, the optical density of these two 50 ml was assessed and the bacterial concentration was confirmed by plating for colony forming units (CFU) on Pseudomonas Isolation Agar (PIA). The bacterial cultures were combined and centrifuged at 9000×g for 10 minutes. The bacterial pellet was resuspended in 5 ml $dH_2O$ and heat-inactivated for four hours at 60° C. After inactivation, 10% of the bacterial suspension was plated on PIA to confirm killing. A Bradford assay was used to determine protein concentration after inactivation, and heat-inactivated bacteria were stored at −20° C. until use.

Outer membrane protein extraction. Outer membrane proteins (OMPs) were isolated from PAO1 using the method described by REW Hancock (Hancock Laboratory Methods. http://cmdr.ubc.ca/bobh/methods/) with the following modifications. P. aeruginosa was grown in LB and bacteria were pelleted by centrifugation for 10 minutes at 8000×g at 4° C. in a RC 5C Plus centrifuge (Sorvall, Thermo Fisher Scientific, Waltham, Mass.) with an SLA-1500 rotor and resuspended in cold 20% sucrose in 10 mM Tris (pH 8.0), then frozen in −20° C. until processing. The bacteria were passed through a Microfluidizer® (Microfluidics Corp., Westwood, Mass.) with a H102 100 μm attachment once to break the cells and then centrifuged at 1800×g for 10 minutes at 4° C. to remove cell debris. A two-step sucrose gradient with 70% and 50% sucrose in 10 mM Tris was used to produce a crude separation of the inner and outer membranes. To do so, the sucrose gradient was centrifuged overnight at 41,474×g with a SW28 rotor (Beckman) in an Optima XL-100K Ultracentrifuge (Beckman Coulter). The outer membrane protein fraction was carefully removed, and this fraction was pelleted by centrifugation for 1 hour at 221824×g in a 50.2 Ti rotor (Beckman) in an Optima XL-100K Ultracentrifuge (Beckman Coulter). The pellet was resuspended in HyClone™ water (HyClone Laboratories, Logan, Utah). Protein concentration was determined by Bradford assay. OMPs were separated by SDS-PAGE and stained with Coomassie blue to visualize protein content and to assess continuity across preparations (FIG. 1a).

Mouse immunization experiments. Six to twelve-week-old C57BL/6 mice were purchased from Charles River (Wilmington, Mass.). Mice were housed in micro-isolators with specific-pathogen free conditions. Food and water were available ad libitum. Groups of mice were immunized intradermally with 1 μg P. aeruginosa OMPs resuspended in HyClone™ water (GE Life Sciences) with 1 μg dmLT diluted in HyClone™ water, 1 μg P. aeruginosa OMPs alone, 1 μg dmLT alone, or saline (0.9% NaCl, Braun Medical) in a total volume of 50 μl. Vaccines were administered three times, two weeks apart.

Western Blot. Ten μg P. aeruginosa OMPs were separated on a 4-20% SDS-PAGE gel (BioRad) alongside a protein molecular weight ladder (BioRad, Hercules, Calif.). After separation, the proteins were transferred from the gel to a nitrocellulose membrane (iBLOT) using the iBLOT system per manufacturer instructions. The membrane was then blocked in 1.5% bovine serum albumin (BSA) in tris-buffered saline with 1% Tween-20 (TBS-T) for 1 hour, then washed and incubated overnight at 4° C. with pooled pre-immune sera or sera from mice immunized with P. aeruginosa OMPs and dmLT. Sera were diluted 1:200 for IgG Western Blots and 1:100 for IgM Western blots. The following day, membranes were washed and incubated for 1 hour with goat anti-mouse IgM (AbCam) diluted 1:2000 in TBS-T or goat anti-mouse IgG (BioRad) diluted 1:3000 in TBS-T. Membranes were washed and developed with the Opti-4CN kit (BioRad) according to manufacturer instructions and imaged using a GE AI600 RBG Imager (GE Healthcare, Waltham, Mass.).

Analysis of antibody responses. Two weeks after the final immunization, mice were sacrificed by $CO_2$ asphyxiation. Blood was collected by cardiac puncture, centrifuged in serum separator tube (BD) at 7,000×g for 10 minutes, and serum was collected and kept at −80° C. until analysis. To collect bronchoalveolar lavage fluid (BAL), the mouse trachea was exposed, and a tracheostomy was performed. A luer stub adaptor (BD) attached to a 1 ml syringe (Fisher) was filled with cold Complete Protease Inhibitor (PI) Cocktail (Roche) and inserted into the trachea that was then tied with thread. The lungs were washed three times with the Complete PI Cocktail and the collected BAL fluid was kept at −80° C. until analysis. Enzyme-linked Immunosorbent Assays (ELISA) were performed to determine antigen-specific IgG concentrations in immunized mice. To perform the ELISAs, flat bottom 96-well polystyrene plates (Costar) were coated overnight at 4° C. with heat-inactivated *P. aeruginosa* at a concentration of 1 µg/well in coating buffer or with purified mouse standards (IgG1, Sigma or IgA, Sigma). Plates were then washed three times with PBS+ 0.5% Tween 20, hereafter referred to as PBS-T. Blocking buffer with 2% skim milk powder in PBS-T was added to the wells for 1 hour. Wells were then washed three times with PBS-T and samples were added in a volume of 100 µl/well. Samples were diluted serially in a dilution buffer of 0.2% skim milk powder with PBS-T. Serum and BAL samples were added to the coated plates, and samples were incubated for 1 hour at room temperature. Plates were washed 3 times with PBS-T. Detection by IgG ELISAs was performed using AKP-conjugated rabbit anti-mouse IgG (Sigma) diluted 1:300 in dilution buffer. Detection by IgA ELISAs was performed using HRP-conjugated goat anti-mouse IgA (Abcam) diluted 1:500 in dilution buffer. Secondary antibodies were added at a volume of 100 µl/well and incubated for 1 hour at room temperature. Plates were then washed 5 times with PBS-T. For detection of IgG, p-nitro-phenyl-phosphate (Sigma) was dissolved in diethanolamine buffer at a concentration of 1 mg/ml and 100 µl of this solution was added to the wells. After development of the assay, the reaction was stopped using 50 µl/well 2M NaOH. Plates were read immediately at 405 nm to determine optical density (OD). For the detection of IgA, TMB Substrate kit (KPL) was used according to the manufacturer's instructions and the reaction was allowed to occur for 2.5 minutes before it was stopped using 1 M $H_3PO_4$. Plates were read immediately at 450 nm to determine OD. Results were expressed as ELISA units/ml (EU/ml) using an average of three sample dilutions closest to the midpoint of the standard curve. Samples in which the OD readings were less than 3 standard deviations above the reading of the blank were considered to be non-responders.

Analysis of T cell responses. Lungs were harvested from a subset of mice (n=3 per group) two weeks after the final immunization. Mice were sacrificed by $CO_2$ asphyxiation and lungs were excised to prepare single cell suspensions as follows. The excised lungs were cut into pieces approximately 1-2 mm in size and placed in 5% RPMI with 0.2 Wünsch units/ml Liberase™ (Roche) then incubated for 1 hour at 37° C. in a shaking incubator at 233 rotations per minute. After incubation, lungs were placed on a 70 µm nylon cell strainer (Fisher) and homogenized with a rubber syringe plunger from a 5 ml syringe (Fisher). The screen was intermittently rinsed with RMPI (Gibco) containing 1% fetal bovine serum (FBS, Atlanta Biologicals). The cell suspension was centrifuged at 460×g for 10 minutes at 4° C. Supernatant was decanted and the cells were resuspended in 2 ml ACK red blood cell lysis buffer (Invitrogen) and incubated at room temperature for 3 minutes with occasional shaking. To stop the reaction, 20 ml of RMPI (Gibco) containing 10% fetal bovine serum (FBS, Atlanta Biologicals), hereafter referred to as 10% RPMI, was added to the cells. Cells were then centrifuged at 300×g for 10 minutes, supernatant was decanted, and the cells were resuspended in 5 ml 10% RPMI. The viable cells were counted on a Cellometer (Nexcelom Bioscience, Lawrence, Mass.) using Trypan Blue (Sigma) then centrifuged at 300×g for 10 minutes and resuspended in a final volume of $1 \times 10^6$ cells/ml.

For the restimulation assay, the following were added to the wells containing 10% RPMI in a volume of 100 µl: 2 mg/ml anti-CD28 antibody, 2 mg/ml anti-CD28 antibody plus 1 mg/ml heat-inactivated *P. aeruginosa*, or 50 ng/ml phorbol 12-myristate 13-acetate (PMA, Sigma) and 1 mg/ml Ionomycin (Sigma) as a positive control. Cells were incubated at 37° C. for 2 hours, then treated with Golgi Plug (Becton, Dickinson & Co. "BD") according to manufacturer's instructions and incubated for an additional 6 hours at 37° C. Cells were then centrifuged for 5 minutes at 300×g, washed with 200 µl phosphate buffered saline (PBS) and resuspended in 50 µl of sorter buffer with 5 µl/ml Fc Block (anti-CD16/CD32, BD) and incubated for 10 minutes. Cells were then stained for viability, and the expression of CD3, CD4, and CD44 on the cell surface for 20 minutes in the dark at room temperature. Stained cells were then washed twice with sorter buffer, fixed and permeabilized using 100 µl/well of Cytofix/Cytoperm™ Solution (BD). After 20 minutes, cells were washed twice with Perm/Wash buffer (BD) and resuspended in antibodies to stain for intracellular IFN-γ and IL-17. After an overnight incubation in the dark at 4° C., cells were washed twice with Perm/Wash buffer (BD), resuspended in sorter buffer, and stored at 4° C. Prior to flow cytometry collection, all samples were filtered through a 100 µm nylon mesh filter. Samples were collected using a BD Biosciences Fortessa cytometer and data were analyzed in FlowJo (BD). Cells were gated using granularity to include lymphocytes, then by size to include only single cells. Cells were then assessed for viability, then expression of CD3 on the surface and exclusion of B220, CD11b, CD11c, CD19, F4/80, and NK1.1 on the surface to confirm T cells. The CD3+B220-CD11b-CD11c-CD19-F4/80-NK1.1-T cell population was then gated to include CD4+ T cells. CD4+ T cells were then gated to include those antigen-experienced (CD44+) cells producing the cytokines IFN-γ, IL-4, or IL-17A. All gating was done using a fluorescence minus one (FMO) technique to confirm negative and positive populations.

Mouse Challenge Experiments. Two weeks after the final immunization, mice were administered *P. aeruginosa* directly to the lungs to induce an acute pneumonia infection. A method of oropharyngeal aspiration was used to administer bacterial inocula to mice (20). Mice were anesthetized with 1-5% isoflurane gas in oxygen continuously. Once fully anesthetized, mice were suspended vertically by the upper incisors on a nylon filament. The nares were pinched with curved forceps and the tongue was gently extracted from the mouth and displaced using blunt forceps. The base of the tongue and pharynx was visualized. A 50 µl suspension of bacteria containing approximately $10^7$ CFU was placed in the posterior pharynx with a micropipetter. The mouse was allowed to aspirate the bacteria for 15 breaths while respiration was monitored to ensure the suspension was fully aspirated. The tongue and nares were released, and mice were allowed to recover in hand, held in a vertical position until fully awake. Mice were closely monitored for 10 days and humanely sacrificed if they reached a moribund state (ruffled fur, shaking, and loss of mobility). At day 10, survivors were euthanized and tissues (blood, lung, spleen) were harvested and homogenized, then plated to determine bacterial cfu. Three independent challenge experiments were performed with an average challenge dose of $1.4 \times 10^7$ CFU (doses ranged from $7.0 \times 10^6$ cfu to $1.6 \times 10^7$ cfu).

For lung cytokine analyses, BAL fluid was collected from a subset of challenged mice (n=5 per group) 24 hours after infection and stored at $-80°$ C. until analysis. The BAL fluid was evaluated by Luminex assay using a murine 25-plex cytokine kit (Millipore) and read on a Bioplex 200 reader (BioRad). Cytokine concentrations, determined as pg/ml, were standardized by BAL fluid protein content, and presented as pg/mg protein.

Statistics. All data were analyzed in GraphPad Prism version 6. Statistical significance was determined using a one way ANOVA with Tukey's multiple comparisons test, a Two-tailed t test, or log rank Mantel-Cox test as indicated in the figure legends. Statistical significance is indicated as ns=not significant, $*p<0.05$, $p<0.01$, $*p<0.005$, $****p<0.0001$.

Example 2

This Example shows that intradermal immunization with P. aeruginosa outer membrane proteins (OMPs) and dmLT promotes anti-pseudomonal IgG in the lung.

Figure 1B:
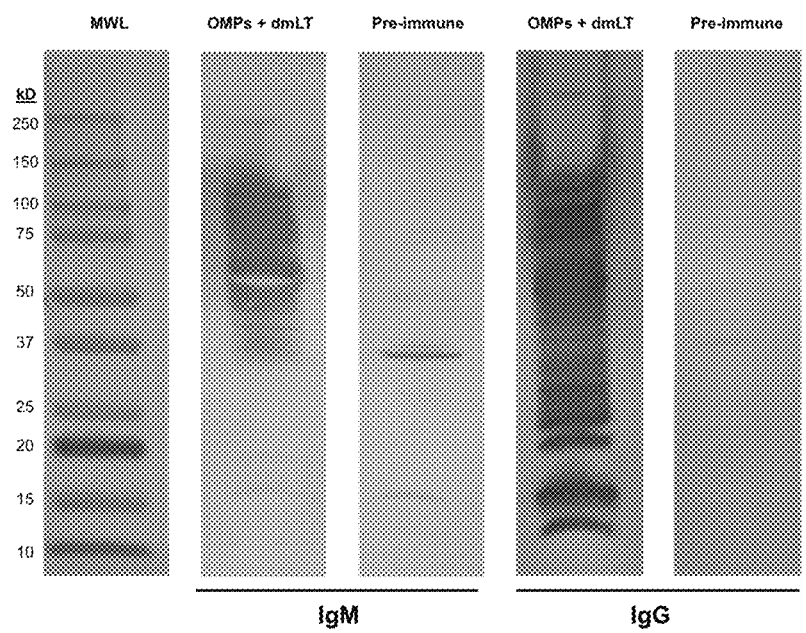
FIG. 1B. Ten micrograms of P. aeruginosa OMPs were probed using pre-immune sera or sera pooled from mice immunized intradermally with P. aeruginosa OMPs+dmLT. Lanes 2-3 were probed with anti-mouse IgM and lanes 4-5 were probed with anti-mouse IgG. MWL=molecular weight ladder.
Figure 2A:
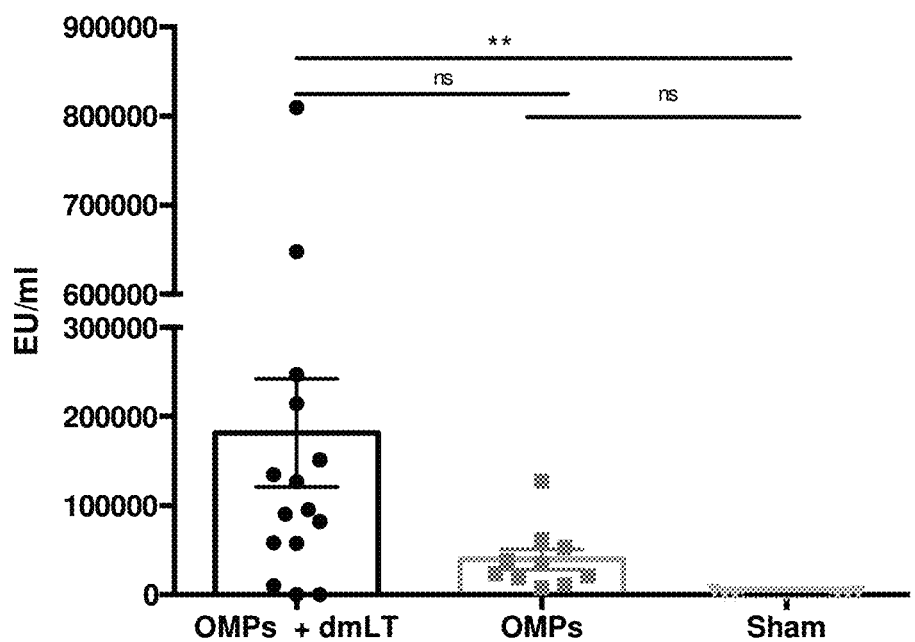
FIGS. 2A and B.
Figure 2B:
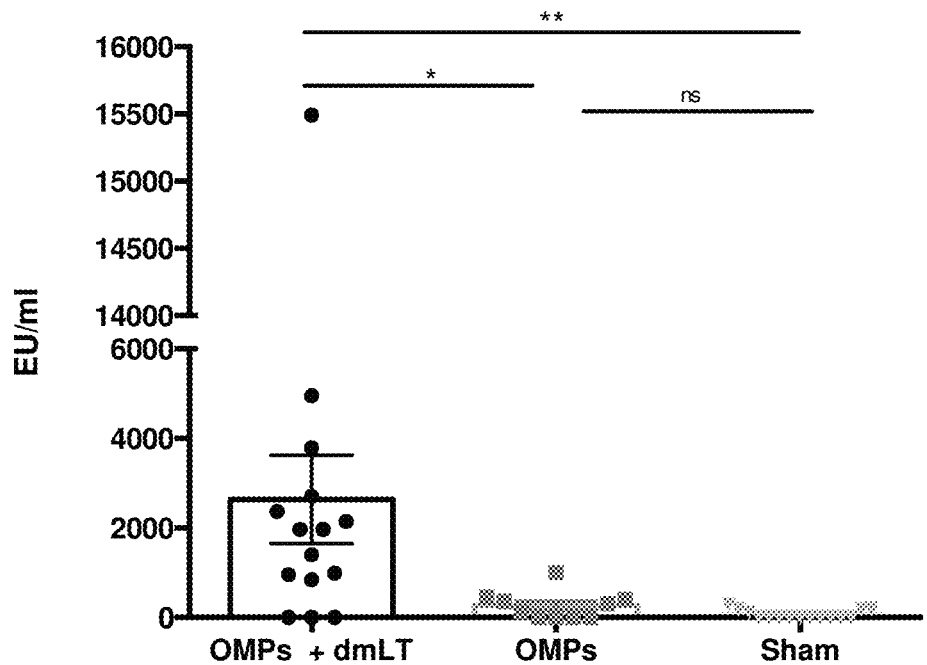
FIG. 2B.

Mice were immunized with dmLT adjuvant combined with P. aeruginosa OMPs (FIG. 1a,b) three times, 14 days apart. Control groups of mice received OMPs alone or saline (sham). Antigen-specific IgG was measured in the serum and BAL fluid by ELISA two weeks after the final immunization. Immunization with P. aeruginosa OMPs plus dmLT induced higher levels of anti-pseudomonal IgG in the serum compared to immunization with OMPs alone (p=0.0505) or sham (p<0.01) (FIG. 2a). Moreover, immunization with P. aeruginosa OMPs and dmLT induced the production of significantly more anti-pseudomonal IgG in the pulmonary environment compared to immunization with OMPs alone (p<0.05) or sham (p<0.01) (FIG. 2b). The antibody responses were directed against multiple protein antigens as indicated by Western blot (FIG. 1b). There was no difference in the levels of antigen-specific IgA in serum and antigen-specific IgA in BAL was undetectable. These results demonstrate that intradermal immunization with P. aeruginosa antigens plus dmLT adjuvant promotes antigen-specific IgG responses in the blood and lung mucosa.

Example 3

This Example shows that intradermal immunization with P. aeruginosa OMPs and dmLT elicits pulmonary IFN-γ+ and IL-17+CD4+ T cells.

Figure 3A:
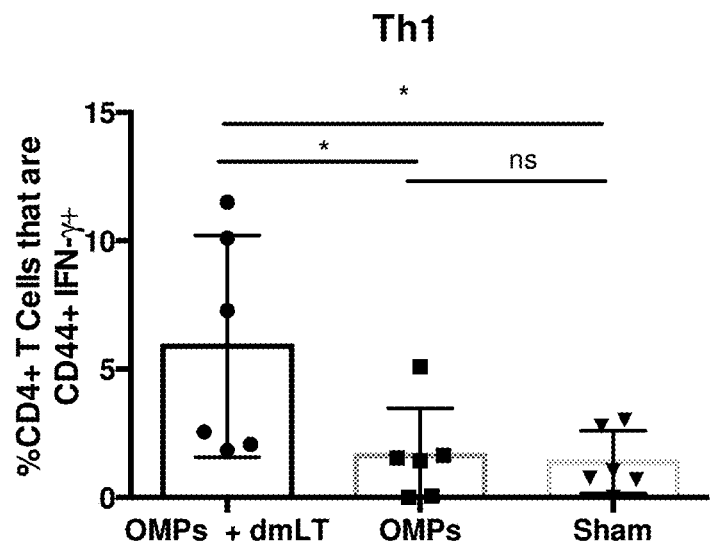
FIGS. 3A, B, and C.
Figure 3B:
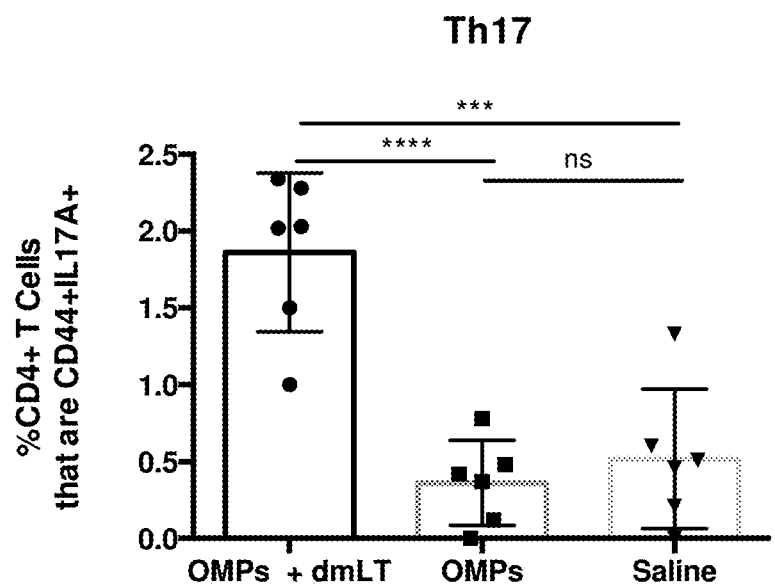
FIG. 3B.
Figure 3C:
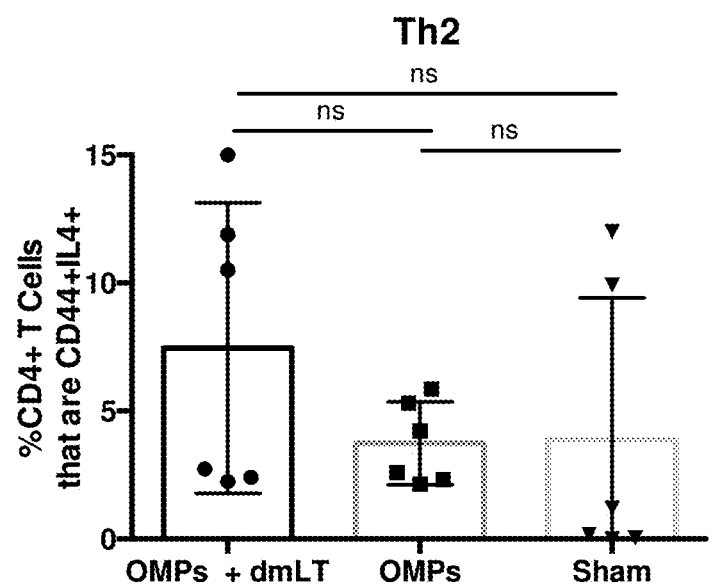
FIG. 3C.

Given that dmLT increased Pseudomonas-specific antibody in the lung, we next examined cellular immune responses elicited by immunization with P. aeruginosa OMPs and dmLT to determine if the inclusion of dmLT adjuvant could increase T cell responses in the lungs of immunized mice. CD4+ T cells were harvested from the lungs of mice two weeks after the final immunization, restimulated with heat-inactivated P. aeruginosa, and analyzed by intracellular cytokine staining and flow cytometry. Mice immunized with P. aeruginosa OMPs plus dmLT possessed a significantly greater percentage of antigen-experienced CD4+ T cells in the lung that produced IFN-γ after restimulation compared to mice immunized with OMPs alone (p<0.01) or sham (p<0.01) (FIG. 3a). Mice immunized with P. aeruginosa OMPs plus dmLT also had a significantly greater percentage of antigen-experienced CD4+ T cells in the lung that produced IL-17A compared to mice immunized with OMPs alone (p<0.05) or sham (p<0.05) (FIG. 3b). There was no significant difference in the percentage of antigen-experienced IL-4 producing CD4+ T cells in immunized mice (FIG. 3c). There was no significant difference in the percentage of lung CD4+ T cells that were CD44+ among the groups. We did not observe any significant differences in the percentage of cytokine-producing antigen-specific CD4+ T cells in the spleens of immunized mice. These results indicate that intradermal immunization with P. aeruginosa OMPs plus dmLT promoted a mixed Th1/Th17-type CD4+ T cell response in the pulmonary tissue itself and that inclusion of dmLT adjuvant was required for achieving this mucosal response.

Example 4

This Example shows that intradermal immunization with P. aeruginosa OMPs and dmLT provides protective immunity against P. aeruginosa.

Figure 4A:
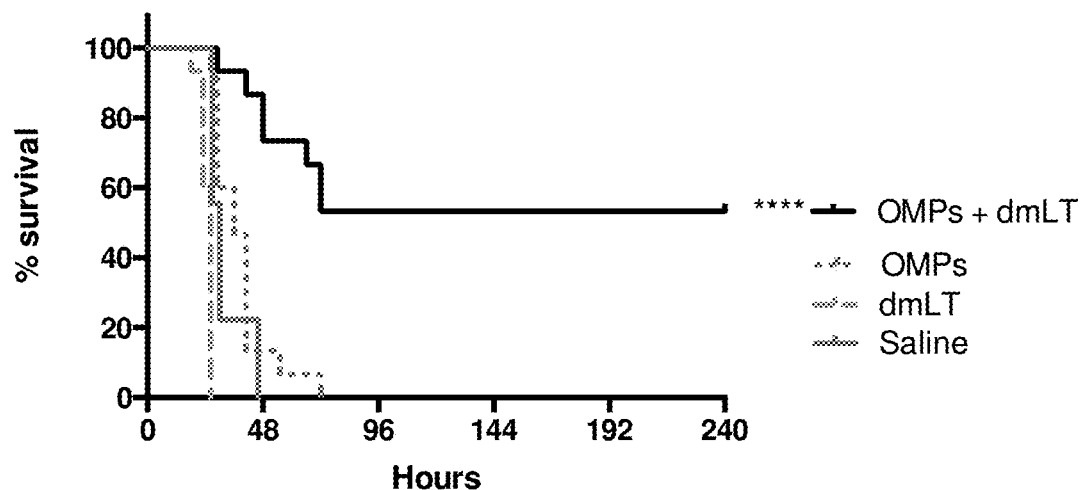
FIGS. 4A and B.
Figure 4B:
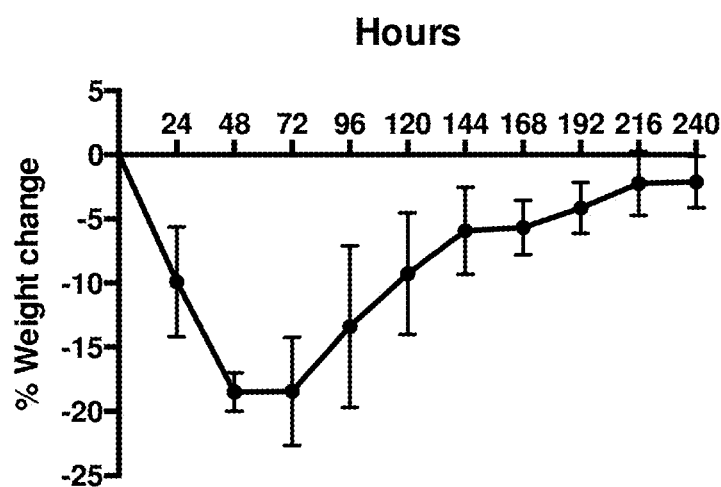
FIG. 4B.

To evaluate the protective efficacy of intradermal immunization with P. aeruginosa OMPs and dmLT against subsequent P. aeruginosa challenge, mice were immunized as above and then challenged with an average dose of $1.4 \times 10^7$ cfu, of P. aeruginosa by oropharyngeal aspiration two weeks after the final immunization. Mice injected with P. aeruginosa OMPs plus dmLT were significantly protected against an otherwise rapidly lethal lung infection (p<0.0001, FIG. 4a). OMPs plus dmLT immunized mice displayed 53% survival over the 10-day study period, whereas mice immunized with OMPs alone, dmLT alone, or sham completely succumbed to infection within 1-3 days. Immunized mice that survived challenge began recovering after day 3 and steadily regained weight (FIG. 4b). All surviving animals were euthanized at the 10-day study endpoint and blood, lung, and spleen homogenates were plated to evaluate bacterial persistence. P. aeruginosa was undetectable in all tissues examined suggesting that surviving mice had cleared the infection.

Example 5

This Example shows that protected mice mount a Th1/Th7-type immune response early during lung infection.

Figure 5A:
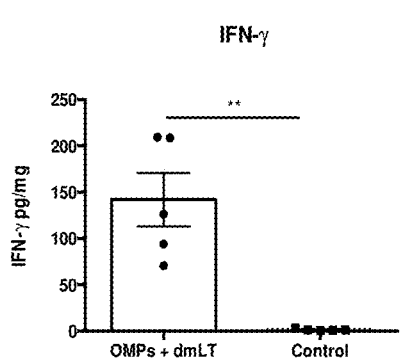
FIGS. 5A-H.
Figure 5B:
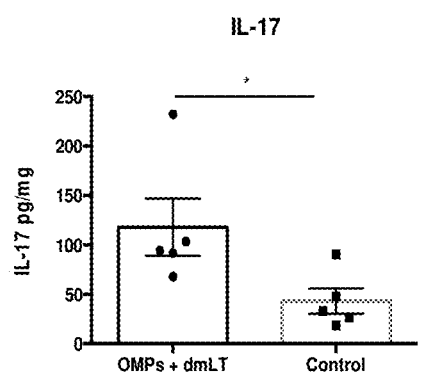
Figure 5C:
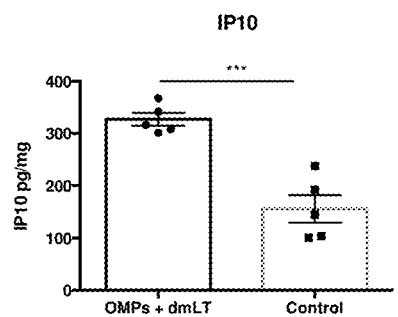
Figure 5D:
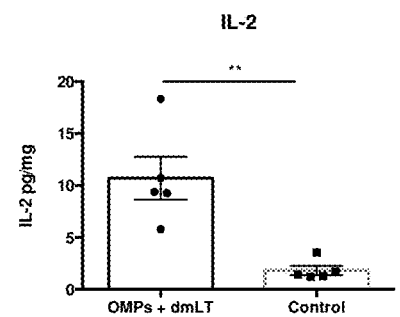
Figure 5E:
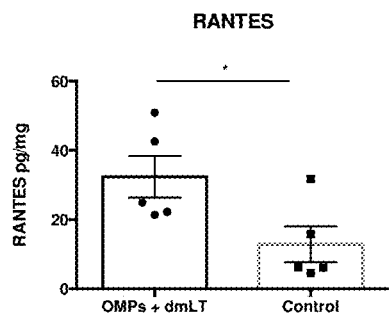
Figure 5F:
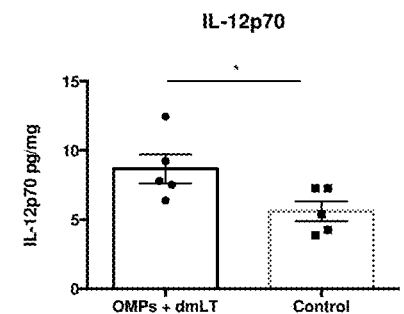
Figure 5G:
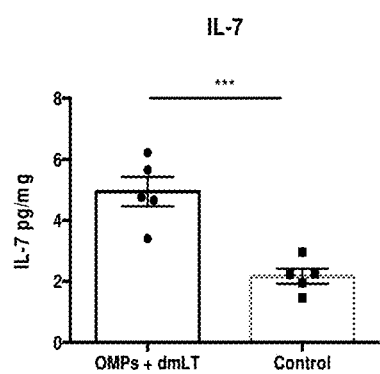
Figure 5H:
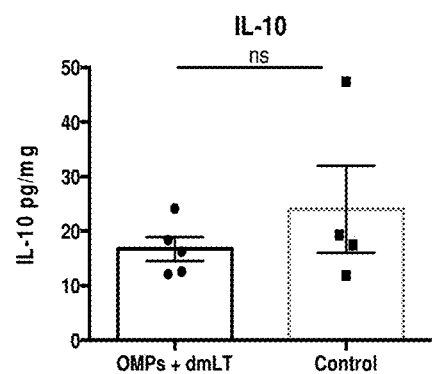
Figure 6A:
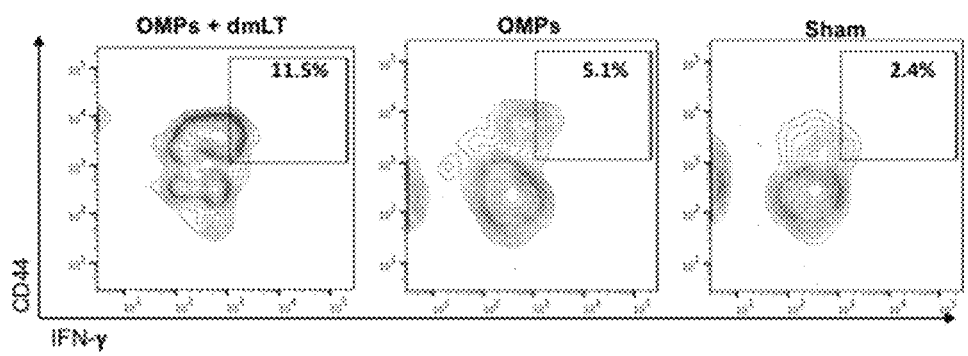
FIGS. 6A, B, and C.
Figure 6B:
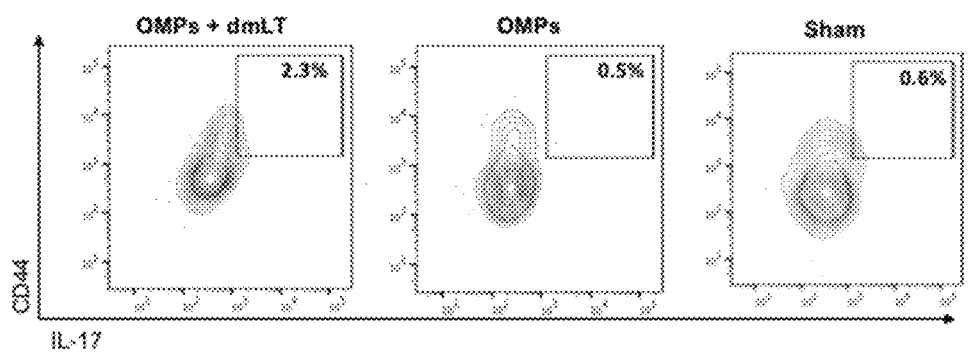
FIG. 6B. Same experiment as reported in FIG. 6A, but the contour plots are representative of examples demonstrating the percentage of CD4+ T cells that are CD44+ and producing IL-17.
Figure 6C:
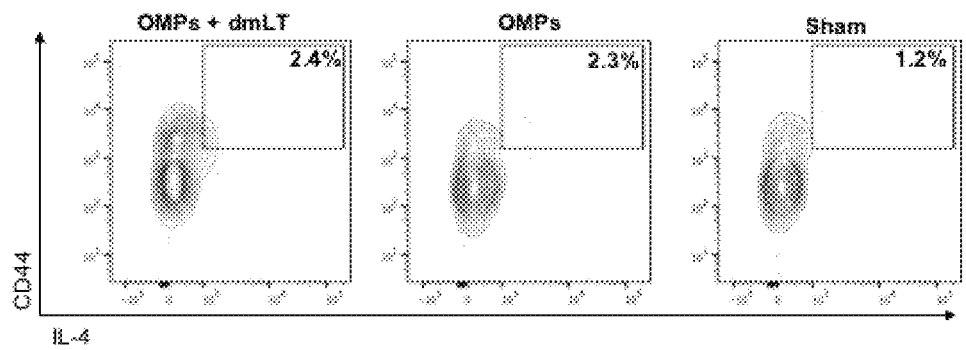
FIG. 6C. Same experiment as reported in FIG. 6A, but the contour plots are representative of examples demonstrating the percentage of CD4+ T cells that are CD44+ and producing IL-4.
Figure 7:
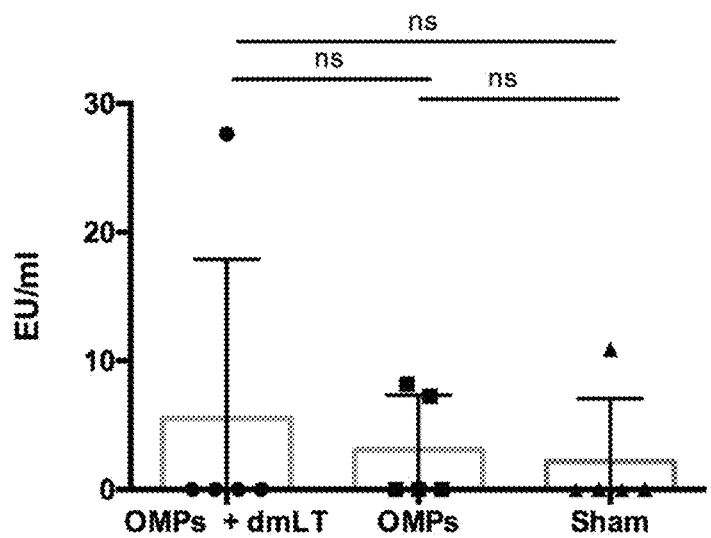
FIG. 7.
Figure 8:
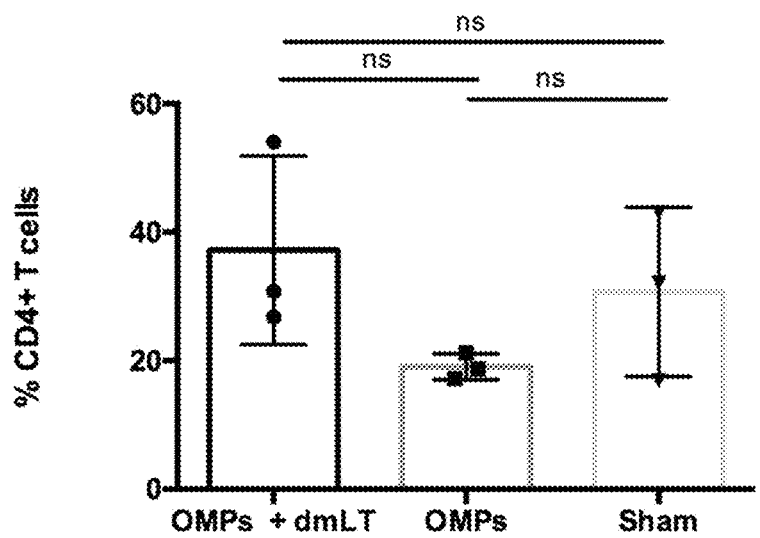
FIG. 8.

Given that intradermal immunization with P. aeruginosa OMPs and dmLT elicits pulmonary IFN-γ+ and IL-17+ CD4+ T cells, we sought to determine if the cytokine profiles in protected immunized mice differed from that of control-immunized mice that succumbed rapidly to P. aeruginosa infection. Mice immunized with OMPs plus dmLT displayed a significant increase in the Th1 cytokine IFN-γ (p<0.01) and the Th17 cytokine IL-17 (p<0.05) in the BAL fluid (FIG. 5a,b) at 24 hours post-infection compared to control mice (dmLT). This was accompanied by an increase in other Th1-associated cytokines, including interferon-γ inducible protein (IP10, FIG. 5c, p<0.0005), IL-2 (FIG. 5d, p<0.01), RANTES (FIG. 5e, p<0.05), and IL-12p70 (FIG. 5f, p<0.05). No significant differences were noted for the Th2-associated cytokines IL-4 and IL-5, or for the anti-inflammatory cytokine IL-10 (FIG. 5h). Additionally, OMPs plus dmLT immunized mice had significantly greater levels of IL-7, a lymphocyte survival cytokine, compared to control mice (p<0.005, FIG. 5g). Taken together, these results demonstrate that immunization with OMPs plus dmLT helps promote a Th1- and Th17-type immune response within the first 24 hours after *P. aeruginosa* lung infection.

Example 6

This Example discusses the results reported in Examples 2-5.

Pulmonary infections remain a significant cause of morbidity and mortality globally. As antibiotic resistance continues to rise among bacteria that cause severe respiratory infections, the development of vaccines that drive protective pulmonary immune responses is critical. In this work, we demonstrate that intradermal immunization with *Pseudomonas* OMPs and dmLT adjuvant elicits cellular and humoral immune responses in the lung and provides protection against an otherwise lethal *P. aeruginosa* pulmonary infection. This is the first study of its kind to include dmLT as an adjuvant in a vaccine against *P. aeruginosa*. The adjuvant dmLT has been shown to promote the production of IFN-γ- and IL-17-producing CD4+ T cells at intestinal mucosal surfaces, but not in the lungs. Frederick et al., Mucosal Immunol. 2018, 11(2):549-561. Several studies have shown that Th1 and Th17 CD4+ T cells are important for vaccine-mediated immunity to pulmonary pathogens, including *P. aeruginosa*, *Mycobacterium tuberculosis*, *Bordetella pertussis*, *Streptococcus pneumoniae*, and *Klebsiella pneumoniae*. In our study, addition of dmLT to *P. aeruginosa* OMP created a vaccine that promoted antigen-specific IFN-γ+ and IL17+CD4+ T cells in the lungs of immunized mice. Following *P. aeruginosa* challenge, the inflammatory response in the lungs of immunized, protected mice was composed of cytokines known to be associated with the homing, migration, and proliferation of effector and memory T cells. Among those, IL-17, which is required for T cell development, has been shown to be protective against *P. aeruginosa* pneumosepsis and intra-abdominal peritonitis when administered as an immunotherapy. In addition, the levels of IFN-γ and IL-17 were significantly elevated in protected animals, supporting the importance of a Th1/Th17-type cellular immune response during acute *P. aeruginosa* lung infection. This balanced Th1/Th17-type response is consistent with previous findings that *E. coli* LT mutants promote the production of IL17 and IFN-γ, resulting in protection against lung infection with the respiratory pathogen *S. pneumoniae* (Lu et al., Clinical Vaccine Immunology, 2010, 17:1005-1012).

Despite decades of research, few *P. aeruginosa* vaccine studies have focused on vaccine-induced cellular immunity and the role of T cells in protection. Live-attenuated vaccines (LAV) can be effective in this regard, and a number of LAV platforms have shown protective efficacy against *P. aeruginosa* in murine models. For example, intranasal immunization with a LAV composed of multiple *Pseudomonas* strains, Habs16/IT3/PAO1ΔaroA, provided 75% protection against intranasal challenge with strain Habs16. The protection observed was mediated by CD4+ T cells and dependent upon IL-17 production. However, safety can be a concern for LAV, as there can be some risk of reversion to wild type virulence or infection from the attenuated strain. This is particularly a concern for use in immunocompromised patient populations, including those who are at the highest risk of developing *P. aeruginosa* pneumonia. A safer alternative to LAV are subunit vaccines, such as those composed of *P. aeruginosa* OMPs. OMPs have received considerable attention as they are immunogenic and highly conserved across bacterial strains. A trivalent recombinant subunit vaccine, composed of PcrV-OprI-Hcp1, provided up to 70% survival in an otherwise lethal acute *P. aeruginosa* pneumonia model (40). Immunization with a recombinant OprF-OprI vaccine adjuvanted with complete Freund's adjuvant (CFA) provided 100% and 50% protection against intranasal challenge with strains PAO1 and PAK, respectively, for up to one week post-infection; however, CFA is highly reactogenic and can cause local tissue necrosis, thereby excluding its utility in human vaccines (41). In our study, OMPs administered intradermally with dmLT adjuvant provided 53% protection against a highly lethal pulmonary challenge. Notably, dmLT has already been shown to be safe in multiple clinical trials and thus has the potential to be included in a new *Pseudomonas* vaccine (42). Taken together, these studies demonstrate the potential for subunit vaccines to promote protective immunity against *P. aeruginosa* in the lung. Moreover, our study demonstrates that protection in the lung can be achieved by parenteral vaccine administration. While many studies have investigated parenteral routes of immunization, they often utilize aluminum salts (i.e. alum) as the adjuvant. Alum is known to polarize immune responses toward Th2, resulting in high antibody titers at the expense of Th1 cellular immune responses. In our study, *P. aeruginosa* OMPs administered with dmLT induced significantly more *Pseudomonas*-specific IgG in the pulmonary airways compared to immunization with OMPs alone. LT and LT mutants have been shown to enhance antigen-specific serum and BAL fluid IgG for numerous pathogens (14, 43-46). The ability of dmLT to support antibody responses in addition to Th1/Th17 type cellular immunity is significant and offers a distinct advantage over alum, particularly for those pathogens that require both arms of the immune response. It is worth noting that in our studies, around 20% of mice failed to seroconvert in response to the vaccine. Other studies have found that this kind of variability, even during potent infections, likely depends on infection or vaccination dose or attributes of the infection or vaccine as well as genetic background, age and overall immunologic state of the animal being infected or vaccinated (47)

The adjuvant dmLT can enhance mucosal immune responses when administered via dermal immunization routes. Efficient antigen delivery to draining lymph nodes and subsequent uptake of antigen by lymph node-resident dendritic cells occurs via a dense network of lymphatic vessels that are more broadly distributed in the dermis than in muscle or subcutaneous spaces. This allows for the rapid and direct migration of intradermally-administered antigen to nearby lymph nodes, subsequent activation of T cells, and T cell migration to the proximal mucosa, including respiratory tissue. Intradermal immunization with *Francisella tularensis* Live Vaccine Strain resulted in higher numbers of lung IFN-γ+CD4+ T cells compared with intranasal immunization. Similarly, intradermal immunization improved the efficacy of a recombinant protein vaccine against *M. tuberculosis* compared to subcutaneous administration. These studies, together with our present findings, indicate that the intradermal route can be key for promoting vaccine-induced immunity in the lung. The majority of vaccines currently licensed in the United States are administered parenterally via the intramuscular route. The ability of intradermal vaccination to drive both humoral and cellular immunity against *P. aeruginosa* in the lung underscores the value of this route for vaccination against pulmonary pathogens.

In summary, our results demonstrate that an intradermal vaccine composed of *P. aeruginosa* OMPs plus dmLT is capable of inducing pathogen-specific antibody, IFN-γ+ and IL17+CD4+ T cells in the lungs of mice. This combination of vaccine-induced humoral and cellular immunity provided protection against an otherwise lethal acute *P. aeruginosa* pneumonia and is consistent with the leading argument that antibodies and CD4 T cells, but not CD8 T cells, are important for protection against this organism. These results indicate that inclusion of dmLT adjuvant in intradermally-administered vaccines can drive protective immunity to the respiratory tract. Intradermally administered OMP+dmLT vaccines should therefore be valuable agents in combating *P. aeruginosa* infections, including in special patient populations such as those suffering from cystic fibrosis or chronic obstructive pulmonary disease.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method of inducing an immune response against a lung infection by *Pseudomonas aeruginosa* in a subject, said method comprising intradermally co-administering to said subject *P. aeruginosa* outer membrane proteins (OMPs) and an *Escherichia coli* heat-labile enterotoxin (LT) with mutations at R192G and L211A ("dmLT").

2. The method of claim 1, wherein said OMPs and said dmLT are co-administered in a single formulation.

3. The method of claim 1, wherein said intradermal administration is by microneedles.

4. The method of claim 1, wherein said *P. aeruginosa* OMPs comprise OprI.

5. The method of claim 1, wherein said *P. aeruginosa* OMPs comprise OprF.

6. The method of claim 1, wherein said *P. aeruginosa* OMPs comprise OprG and KatA.

7. The method of claim 1, in which said *P. aeruginosa* OMPs and said dmLT are co-administered to a subject who does not have a *P. aeruginosa* lung infection.

8. The method of claim 7, wherein said subject has cystic fibrosis.

9. The method of claim 7, wherein said subject is on a ventilator.

10. The method of claim 1, in which said *P. aeruginosa* OMPs and said dmLT are co-administered to a subject who has a *P. aeruginosa* lung infection.

11. The method of claim 10, wherein said subject has cystic fibrosis.

12. The method of claim 10, wherein said subject is on a ventilator.

13. A composition for intradermal vaccination of a subject in need thereof, said composition comprising *Pseudomonas aeruginosa* outer membrane proteins (OMPs) and an *Escherichia coli* heat-labile enterotoxin (LT) with mutations at R192G and L211A ("dmLT").

14. The composition of claim 13, further comprising a pharmaceutically acceptable carrier.

15. The composition of claim 14, further wherein said *P. aeruginosa* OMPs include OprI.

16. The composition of claim 13, wherein said *P. aeruginosa* OMPs comprise OprF.

17. The composition of claim 13, wherein said *P. aeruginosa* OMPs comprise OprG and KatA.

18. The method of claim 1, wherein said immune response is induction of pulmonary IL-Th17+ CD4 T-cells in said subject.

19. The method of claim 1, wherein said immune response is induction of pulmonary IFN-γ in said subject.

20. The method of claim 1, wherein said immune response is induction of pathogen-specific antibodies in said subject.

* * * * *